United States Patent [19]
Collet-Beillon

[11] Patent Number: 5,574,801
[45] Date of Patent: Nov. 12, 1996

[54] METHOD OF INSPECTING AN ARRAY OF SOLDER BALL CONNECTIONS OF AN INTEGRATED CIRCUIT MODULE

[76] Inventor: Olivier Collet-Beillon, 27 Avenue de Brimont, 78400-Chatou, France

[21] Appl. No.: 289,972

[22] Filed: Aug. 12, 1994

[30] Foreign Application Priority Data

Sep. 17, 1993 [EP] European Pat. Off. ............ 93480113.5

[51] Int. Cl.[6] ...................................................... G06K 9/00
[52] U.S. Cl. .......................................... 382/150; 382/148
[58] Field of Search ..................................... 382/150, 256, 382/144, 145, 146, 147, 148, 149, 141

[56] References Cited

U.S. PATENT DOCUMENTS

| | | | |
|---|---|---|---|
| 3,721,825 | 3/1973 | Rasmussen, Jr. ........................ | 250/308 |
| 4,296,474 | 10/1981 | Hurt ........................................ | 364/560 |
| 4,677,473 | 6/1987 | Okamoto et al. ....................... | 348/126 |
| 4,688,939 | 8/1987 | Ray ......................................... | 356/237 |
| 5,058,178 | 10/1991 | Ray ......................................... | 382/141 |
| 5,108,024 | 4/1992 | Kazem-Goudarzi et al. .......... | 228/104 |
| 5,134,665 | 7/1992 | Jyoko ..................................... | 382/150 |
| 5,137,362 | 8/1992 | LeBeau .................................. | 382/145 |
| 5,161,202 | 11/1992 | Kitakado et al. ....................... | 382/147 |
| 5,368,217 | 11/1994 | Simmons et al. ...................... | 228/6.2 |
| 5,376,790 | 12/1994 | Linker et al. ........................... | 250/306 |
| 5,394,246 | 2/1995 | Sugawara ............................... | 356/394 |

FOREIGN PATENT DOCUMENTS

| | | |
|---|---|---|
| 471196A2 | 7/1991 | European Pat. Off. . |
| 472041A2 | 8/1991 | European Pat. Off. . |

OTHER PUBLICATIONS

W. E. Blanz, et al., "Image Analysis Methods for Solder Ball Inspection in Integrated Circuit Manufacturing" IEEE, pp. 509–514, 1987.

Disclosed Anonymously No. 33317, "Solder Ball Connection (SBC) Co–Planarity with X–Ray Technology" Havant GB, Jan. 1992.

*Primary Examiner*—Joseph Mancuso
*Assistant Examiner*—Jayanti K. Patel

[57] ABSTRACT

A method of inspecting an array of balls used as connections in integrated circuit modules such as Solder Ball Connection modules, by means of an inspection apparatus that includes a microprocessor (34), a support (32) for holding in place the modules to be inspected (30), the microprocessor controlling a vertical camera (38) and a tilted camera (40) for obtaining images of the balls, wherein said method includes measuring the X and Y coordinates of each ball of the array to determine a best fitting grid of the balls, detecting the Z coordinate of each ball to determine the best fitting plane for the array of balls, offsetting the best fitting plane such that the offset plane also includes the lowest ball of the array, computing the deviation between each ball and the offset plane, and comparing the computed deviations with predetermined specifications to ascertain whether the inspected module is in compliance with the specifications.

17 Claims, 6 Drawing Sheets

FIG. 5A  FIG. 5B  FIG. 5C
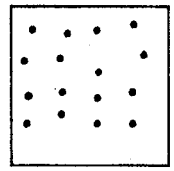 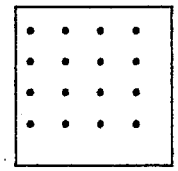 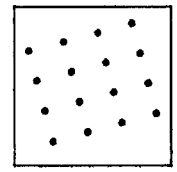
FIG. 6
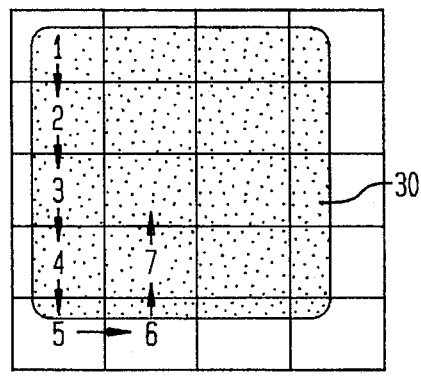
FIG. 7
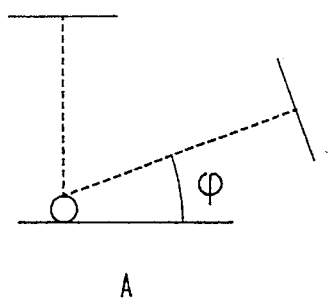 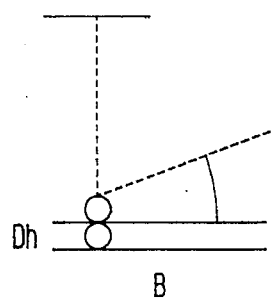 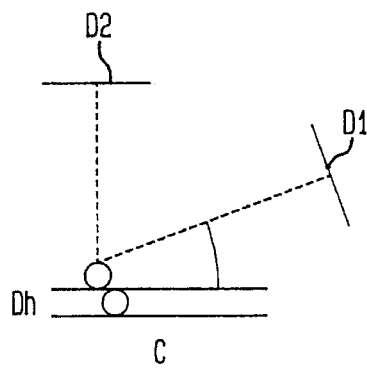
A  B  C

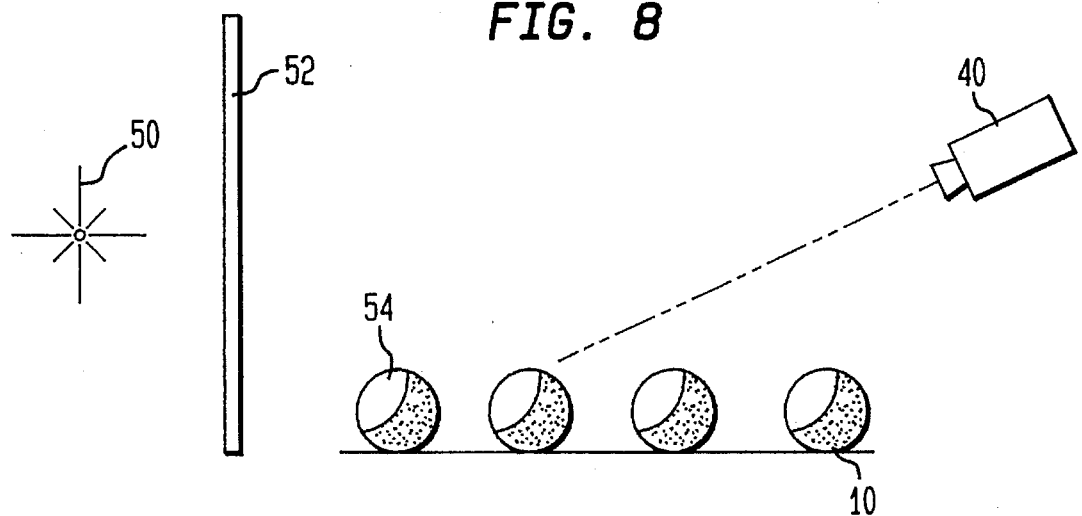
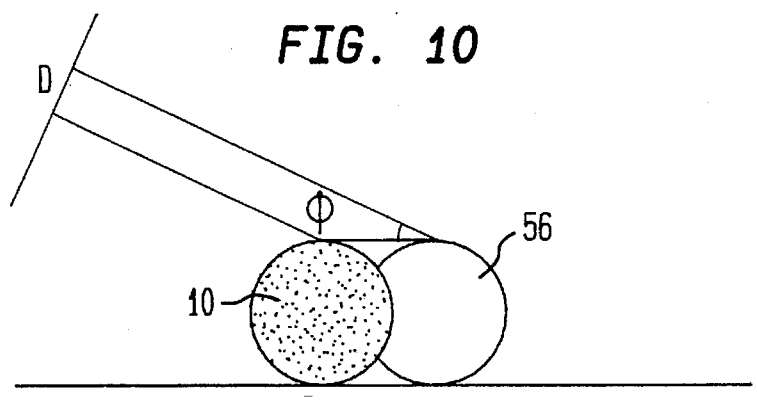

METHOD OF INSPECTING AN ARRAY OF SOLDER BALL CONNECTIONS OF AN INTEGRATED CIRCUIT MODULE

FIELD OF THE INVENTION

The invention relates to a method of inspection used in the manufacture of integrated circuit modules, and more particularly to a method of inspecting an array of solder ball connections used for outside connections in an integrated circuit module in order to determine if the inspected module meets the manufacturing specifications.

BACKGROUND OF THE INVENTION

In many integrated circuit modules and in particular in SBC (Solder Ball Connection) modules, solder balls replace conventional connection pins. The substrate generally includes a plurality of layers which interconnect the chips to solder balls used as input/outputs. Such modules are routinely soldered to a printed circuit board by means of a matrix of conductive pads.

The overall reliability of the bonds created by the soldered ball process is adversely affected by defective balls. By way of example, if a ball has an insufficient height, no electrical connection exists between the ball and its corresponding pad on the circuit board.

In the past, several types of bonding inspection apparatus have been proposed. For instance, U.S. Pat. No. 4,688,939 describes an inspection apparatus of solder bumps by placing a chip carrier on a platform beneath a light ring which is coupled to a television camera. Light directed at an angle towards the sides of the chip carrier is reflected upwardly into the camera by the solder bumps. The output signal of the camera, which varies with the intensity of the light reflected from the bumps, is processed by a visual system to obtain a one-dimensional plot of the light intensity. The one-dimensional plot is analyzed automatically by the system to detect missing or excessive solder bumps on the chip carrier.

In a second illustration, U.S. Pat. No. 5,058,178 relates to an apparatus wherein defective or missing solder bumps of a chip carrier are detected by first illuminating the carrier with dark field illumination. The image of the surface is captured by a television camera. The image is processed to detect defects by first creating a window within the image about each group of solder bumps and creating a bounding box for each bump in each window. Each set of attributes includes the number, size and location of both the windows and the boxes within each window; and similarly, the dimensions, shape and brightness of the image within each box. The value of each attribute is compared to a reference value that represents the attribute when no defects are present. If the attribute differs by more than a predetermined tolerance, it indicates the presence of a defect.

Present state of the art inspection apparatus check each solder bump and verify whether the bump meets the requirements that determine the presence or the absence of a defect. None of the present apparatus inspect the complete array of bumps (or balls) to determine whether they are correctly placed with respect to each other within the array.

OBJECT OF THE INVENTION

Accordingly, it is an object of the invention to provide an automatic method of inspecting an array of balls used as connections in an integrated circuit module to determine whether the module meets its manufacturing specifications.

Another object of the invention is to provide an automatic method of inspecting the centrality and the flatness of an array of balls used as connections in an integrated circuit module.

Still another object of the invention is to provide an automatic method of inspecting an array of balls used as connections in an integrated circuit module by checking the alignment and the flatness of the balls without utilizing an absolute reference, such as the edge of the substrate.

SUMMARY OF THE INVENTION

Accordingly, the present invention relates to a method of inspecting an array of balls used as connections of integrated circuit modules, using an inspection apparatus having a microprocessor, a support for holding in place the module to be inspected, wherein positioning of the support is controlled by the microprocessor, at least one camera connected to the microprocessor, the camera providing images of the balls, the balls being illuminated by a light source. The method, according to the present invention, includes measuring the X and Y coordinates of each ball forming the array of balls to determine the best fitting grid of the balls, detecting the Z coordinate of each ball to determine a best fitting plane for the array of balls, offsetting the best fitting plane to ensure that the offset plane includes the lowest ball of the array, computing the deviation between each ball of the array and the offset plane, and comparing the computed deviation against a predetermined specification to determine whether the module is in compliance with the specification.

BRIEF DESCRIPTION OF THE DRAWINGS

The objects, features and advantages of the subject invention will become more evident with the following description read in connection with the accompanying drawings wherein:

FIGS. 5A–C illustrate three examples of ball arrays which can be inspected with the inspection method, according to the present invention;

FIG. 6 shows successive views of groups of balls that are recorded using the method that determines the centrality of the array of balls;

FIG. 7 shows three representations showing the deviations to be taken into account when the height of the balls is determined;

FIG. 8 shows a schematic diagram of the system used in determining the flatness of the array of balls used in the inspection method, according to the present invention;

FIG. 10 illustrates the correction to be introduced in the determination of the height when the ball is not at its theoretical position;

DETAILED DESCRIPTION OF THE INVENTION

Figure 1:
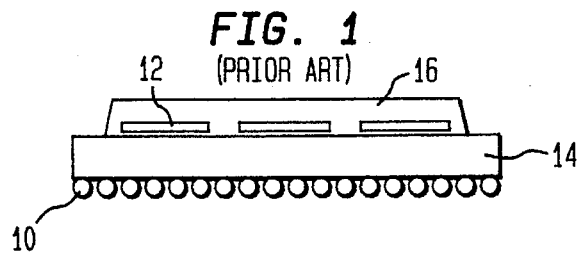
FIG. 1 shows a schematic diagram of a module that uses Solder Ball Connections.
Figure 2:
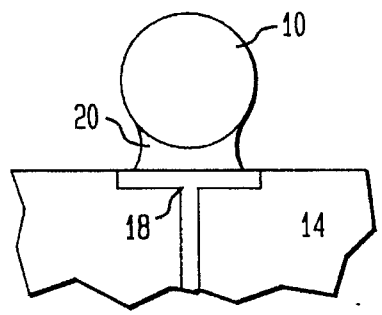
FIG. 2 shows a cross-section of a ball soldered to the pad of the module substrate.

The module to be inspected is generally a Solder Ball Connection (SBC) module shown in FIG. 1. Solder balls 10 replace the conventional pins used for the connections. Substrate 14 contains a plurality of circuitry layers which connect chips 12 to the balls, which are used as input/output terminals. The chips are encapsulated by cap 16. As shown in FIG. 2, each ball 10 is connected to a pad 18 of substrate 14 by a point of solder 20.

Figure 3:
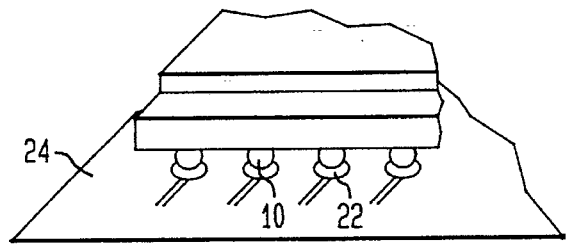
FIG. 3 is a schematic of the module soldered to a printed circuit card.

Several modules are attached to a printed circuit board by soldering the balls on the receiving pads 22 of the board 24 as shown in FIG. 3. If the array of balls soldered on the module is not planar, some balls 10 may be too far removed from pad 22 to be soldered thereto, and no connection to the board is achieved. Furthermore, if the matrix of balls is not regular, some balls may not face their corresponding pad, and again no connection will ensue.

METHOD OF INSPECTION

Figure 4:
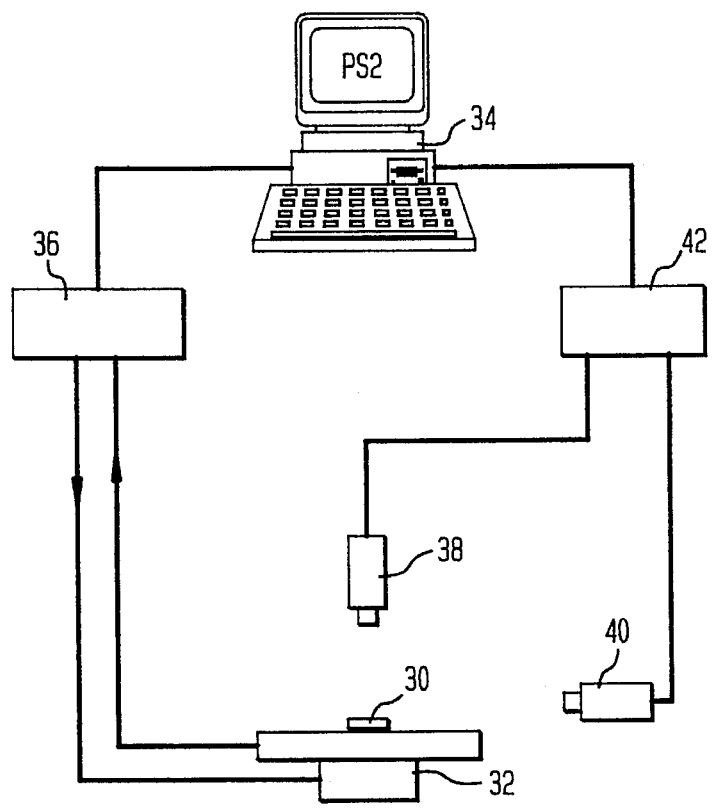
FIG. 4 is a bloc diagram of the system used in the inspection method according to the present invention.

The method of inspection according to the present invention enables the array of balls to be inspected with high degree of accuracy and speed. Such a method achieves its best results when used with the inspection apparatus illustrated in FIG. 4. A module 30 is placed on a motorized table or support which is movable along its X and Y axes. The motion of table 32 is controlled by microprocessor 34 (e.g., an IBM PS/2) via control unit 36. The table can be moved so that the X and Y coordinates of the modules can be adjusted with precision.

Two cameras 38 and 40 are used to perform an inspection of the positioning of the ball in the X,Y plane and height with respect to the horizontal plane. As will be described hereinafter, camera 38 is used to measure the centrality of the ball array, whereas camera 40 is used to sense the flatness of the array. The two cameras 38 and 40 are coupled to a controller 42 which is connected to microprocessor 34. Controller 42 processes the vision algorithms, computes the results, adjusts the light intensity, and selects the camera. Microprocessor 34 performs all controls, synchronizes the axes motion with the vision process and is used to interface with the operator.

The first step of the inspection consists in checking the uniformity of the array of balls, i.e., measuring the centrality of the array. The principle is not to sense the position of each ball with respect to an absolute reference, such as the edge of the substrate, but to define the relative position of each ball in the array with respect to other balls forming the array. Thus, three modules A, B, and C are illustrated in FIG. 5. The first module A has an array forming an irregular matrix. Such a module will be discarded. Conversely, module B has a shifted matrix of balls, and module C has a tilted matrix of balls; these modules B and C can be kept since, in both instances, the matrix of balls is regularly shaped.

More particularly, the step consists in measuring accurately the position of each ball, computing a best fitting grid which is a theoretical grid matching at best all the balls, and computing the deviation between each ball against its theoretical position in the best fitting grid. Such a measure is achieved by means of the vertical camera 38 (see FIG. 4) which takes successive views of the array in the manner illustrated in FIG. 6, wherein the module 30 is shown in grey. Each view 1, 2, 3, . . . 6, 7 corresponds to a matrix of m×n balls. Thus, one view can take the image of 20 balls corresponding to a 4×5 matrix. The parameters m and n are determined by the distance which the table carrying the module is moved to whenever a new view is required. The technique of taking views in this manner is sometimes called "Boustrophedon", and results in scanning the whole module in a minimum amount of time.

The views are then combined to form a composite image of the module. This can, potentially, create difficulties due to the misalignment of the camera with respect to the table. Such a problem resulting from an image "drift" is solved by a calibration step which will be described hereinafter.

The image magnification and the scale depend on the distance object/camera. Thus, if the distance grows, the magnification becomes smaller. The specifications on the thickness of the module are large, e.g., 0.9 mm. The scales, however, can lead to erroneous results if the difference is as small as 0.1 mm. Thruput considerations preclude calibrating the tool for each module. Therefore, the distance module/camera must be adapted to a predetermined scale which is applicable to each module. The apparatus performing the inspection uses two cameras with different viewing angles resulting in the ability of processing stereo-vision to detect variations in height. Two views are processed from the same object and 3D information is computed. This information is compared with information stored during the calibration step described hereinafter. The Z axis is automatically adjusted to maintain the height between the camera and the module constant. Such a method enables determining a deviation of the order of 10 µm.

As illustrated in FIG. 7, the difference in height for each module is easily determined with the help of the two cameras. In diagram A, there is no height difference; therefore no adjustment is necessary. In diagram B, the height difference Dh is determined by measuring the deviation D1 determined by the tilted camera.

$$Dh = \frac{D1}{\cos\phi}$$

In diagram C, in addition to the difference in height, there is also a difference D2 in the position detected by the vertical camera. In such a case, the height difference is:

$$Dh = \frac{D1 + D2 \cdot \sin\phi}{\cos\phi}$$

When the height difference has been accurately determined by measuring several balls and taking the average, the vertical camera is moved by the distance Dh before further processing.

Figure 9:
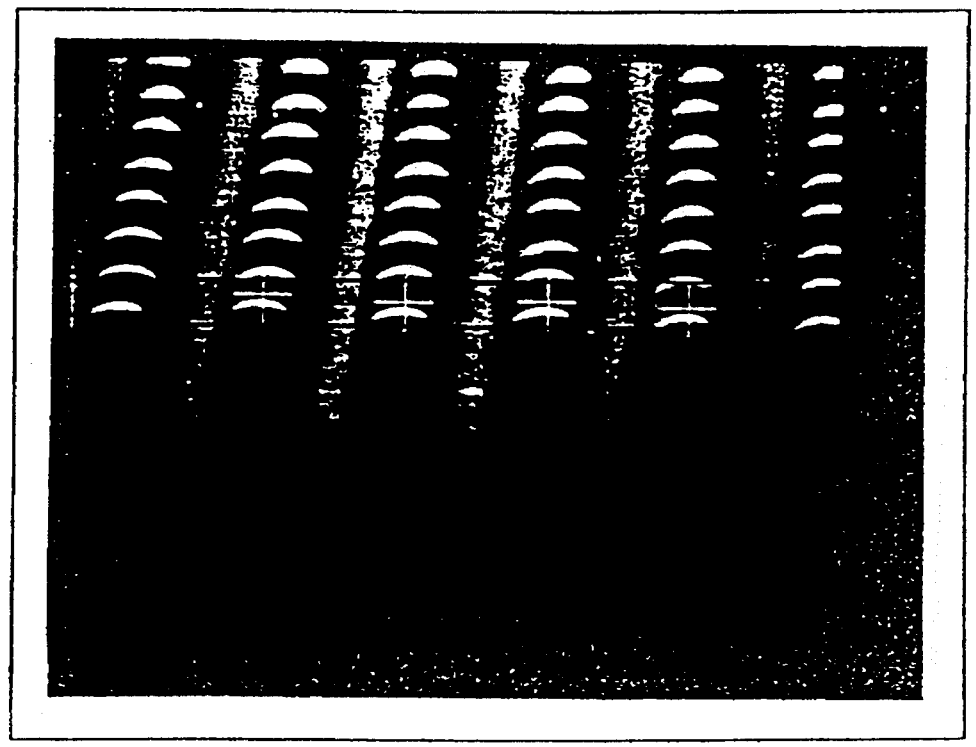
FIG. 9 is a photograph showing the view of the illuminated balls, according to the method of the present invention.

The height of the balls is determined by taking a view for each group of four balls. As shown on FIG. 8, a light source 50 is located opposite camera 40. In order to obtain a diffused light, a diffuser 52 is placed between the light source 50 and the balls 10. With such a light system, it is very easy for the camera to capture a view of the light reflection 54 at the top of the balls, as illustrated in FIG. 9 by the four crosses shown on top of the four balls.

For each ball, a correction of the height is necessary because ball 10 is not at its theoretical position 56, as shown in FIG. 10. Such a deviation with respect to the theoretical Y coordinate is known by measuring the alignment of the balls and determining the theoretical grid, as already described. The correction to be applied to the view is:

$$D = L \sin \Phi,$$

wherein Y is the angle of the camera and L the deviation of the ball with respect to its theoretical position.

The table is then moved to take a view of the next four balls. The technique of taking the views of the balls (Boustrophedon) is the same as it was for measuring the alignment of the balls.

Once the height of the balls forming the array has been determined, corrected and stored, a plane fitting at most the top of the balls, called hereinafter the "best fitting plane", is computed using the Least Square Regression technique. If $X(i,j)$, $Y(i,j)$, and $Z(i,j)$ are the coordinates of each ball top, the equation of a plane including such a point is:

$$Z_{plane} = a.X(i,j) + b.Y(i,j) + c$$

The squared distance between any object and the plane is given by:

$$E(i,j) = [Z_{plane} - Z(i,j)]^2$$

The process consists in computing three parameters of the plane which minimizes the sum of the squared distances, i.e.,:

$$D = \text{sum } E(i,j),$$

wherein D is derived with respect to the three unknown coefficients a, b, c, and the derivatives equal to zero.

Let it be defined:

$$S = Z_{plane} - Z(i,j)$$

$$S = a.X(i,j) + b.Y(i,j) + c - Z(i,j)$$

Therefore, $$dE(i,j)/d^* = 2.dS/d^*.S,$$

wherein * represents any one of a, b, c.

$$dE(i,j)/da = 2.X(i,j).[a.X(i,j) + b.Y(i,j) + c - Z(i,j)]$$

$$dE(i,j)/db = 2.Y(i,j).[a.X(i,j) + b.Y(i,j) + c - Z(i,j)]$$

$$dE(i,j)/dc = 2.[a.X(i,j) + b.Y(i,j) + c - Z(i,j)]$$

These expressions are summed over the working set comprising n objects, and the results are equated to zero.

$$S1 = \text{sum } X \quad S4 = \text{sum } X^2 \quad S6 = \text{sum } X \cdot Y$$
$$S2 = \text{sum } Y \quad S5 = \text{sum } Y^2 \quad S7 = -\text{sum } X \cdot Z$$
$$S3 = -\text{sum } Z \quad \quad \quad \quad \quad \quad \; S8 = -\text{sum } Y \cdot Z$$

This results in:

$$0 = a.S4 + b.S6 + c.S1 + S7 \quad (1)$$

$$0 = a.S6 + b.S5 + c.S2 + S8 \quad (2)$$

$$0 = a.S1 + b.S2 + c.n + S3 \quad (3)$$

Let $$(1).S6 - (2).S4 \quad (4)$$

$$0 = b.(S6.S6 - S5.S4) + c.(S1.S6 - S2.S4) + (S7.S6 - S4.S8)$$

$$(2).S1 - (3).S6 \quad (5)$$

$$0 = b.(S5.S1 - S2.S6) + c.(S1.S2 - n.S6) + (S8.S1 - S3.S6)$$

Let it be further defined:

$$A = (S6 \cdot S6 - S5 \cdot S4) \quad C = (S7 \cdot S6 - S4 \cdot S8) \quad E = (S1 \cdot S2 - n \cdot S6)$$
$$B = (S1 \cdot S6 - S2 \cdot S4) \quad D = (S5 \cdot S1 - S2 \cdot S6) \quad F = (S8 \cdot S1 - S3 \cdot S6)$$

Equations (4) and (5) become $$0 = b.A + c.B + C$$

$$0 = b.D + c.E + F$$

Let $$(4).E - (5).B$$

$$0 = b.(A.E - D.B) + (C.E - F.B)$$

Then coefficient b is given by:

$$b = -(C.E - F.B)/(A.E - D.B)$$

It follows that:

$$a = -(b.S6 + c.S1 + S7)/S4, \text{ and}$$

$$c = -(B.D - A.E)/(D.C - A.F)$$

The deviations between the balls of the array and the best fitting plane are then computed. The best fitting plane is offset so that the new plane, i.e., the inspection plane, includes the top of the lowest ball in the array. Again, the deviations between the balls and the inspection plane are computed. Finally, the computed deviations are compared with the specifications. If they compare favorably, the module is accepted; otherwise, the module is discarded.

THE CALIBRATION PROCESS

Since the apparatus for performing the process according to the invention is an alignment tool, the calibration is particularly important. It consists in determining the ratio camera pixel/real size. This ratio is called "scale" and depends on the optical magnification.

Figure 11:
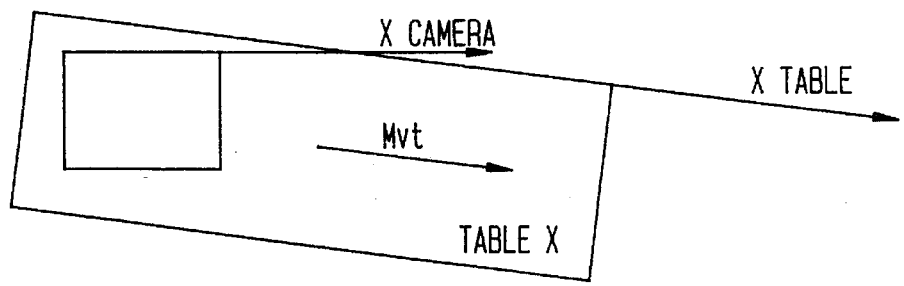
FIG. 11 illustrates a misalignment between the camera and the table carrying the module to be inspected.

Preferably, a CCD (coupled charge device) camera is used. In such a camera, a pixel is not square, so the scale for the two axes X and Y has to be determined. Furthermore, with one axial motion being executed between two image acquisitions, one must also take into account the drift resulting from the misalignment between axes of the camera and the table, as shown in FIG. 11.

Calibration is achieved in two steps: a coarse calibration and a fine calibration. During coarse calibration, one image is snapped (20 balls for centrality and 4 balls for flatness) to determine the approximate pixel scale. The average of the deviation between the balls is computed by combining them two by two.

The fine calibration gives, with high accuracy, the scales X and Y. It also provides the drifts X and Y for centrality measurements. These are obtained using a vertical camera (Note: if the X and Y table axes are not perpendicular, drift X is different from drift Y). For flatness measurements, the camera is tilted at an angle of about 15° with respect to the horizontal plane. The calibration provides the Z scale and the reference for the Z axis, i.e., the distance between the module and the vertical camera used for the centrality.

To perform a fine calibration, the complete module is preferably processed by the inspection method according to the invention using the scale resulting from the coarse calibration.

Figure 12:
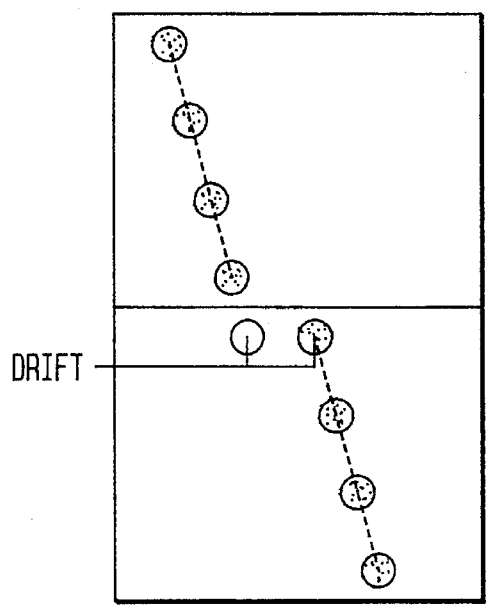
FIG. 12 shows a pair of juxtaposed views that includes drift between first and second views.

Drift is illustrated in FIG. 12 showing two successive views. The slope of the module is computed by averaging all the balls of each view over all the views. Such a slope is called a "correction" (CORR). The variation from one view to the next (VARI) is averaged over all the balls located at the image edges.

$$DRIFT=VARI\ (x,y)-CORR\ (x,y)$$

Figure 13:
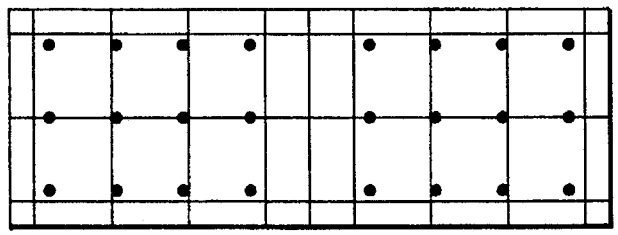
FIG. 13 shows two juxtaposed views separated by a gap caused by a scaling problem.

As far as the scale is concerned, such a problem is illustrated in FIG. 13 showing two views separated by a gap due to a scale problem. This problem is easily solved by noticing that R is not only the ratio of the value of the distance between the balls of the views but it is also the ratio of the "used scale" over the "real scale". Therefore, once R is computed, one may easily rectify the scale. It must be noted that the distances between balls are averaged over the complete module.

Figure 14:
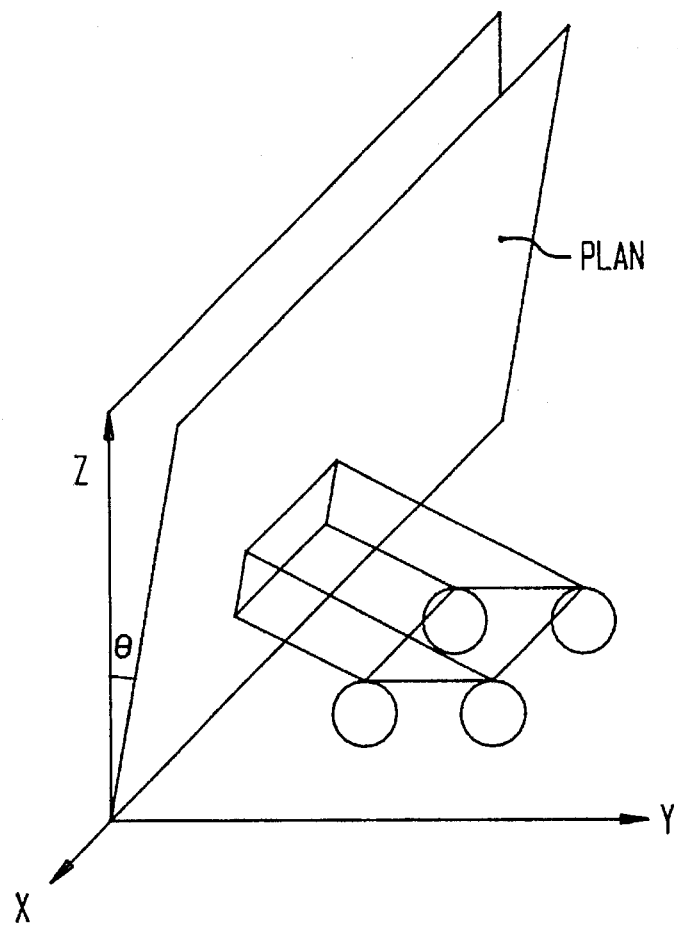
FIG. 14 illustrates the deviation between the image plane and the vertical plane in determining the Z scale.

For measurement of the flatness, the Z scale needs to be determined. The angle θ between the image plane and the vertical plane must be computed, as illustrated in FIG. 14. If RS is the real scale and SS the observed scale, the following equations can be set:

$$RS(X)=SS(X)$$

$$RS(Y)=SS(X).R$$

$$\sin\theta = \frac{SS(Y)}{RS(Y)}$$

$$\text{Scale }(Z) = \frac{RS(Y)}{\cos\phi}$$

Figure 15:
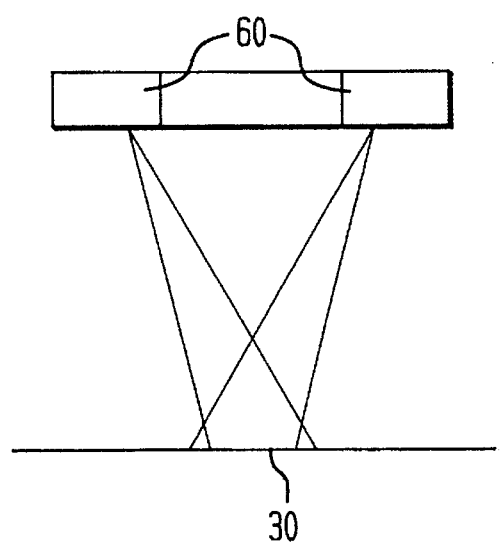
FIG. 15 shows the light ring used as the light source of the inspection method, according to the present invention.

With reference to FIG. 15 it must be noted that, in order to obtain an image that includes the balls without any shadow (which could disturb the measuring process), a non-directed and homogeneous light source 60 called a "light ring" is used to illuminate module 30 during the inspection process. Such a light ring composed of LEDs 100 is highly advantageous in that it does not provide much heat which would constitute a nuisance for achieving inspection.

While the invention has been described with respect to a particular embodiment thereof, it will be apparent to those skilled in the art that variations may be made therein without departing from the spirit and the scope of the present invention.

What is claimed is:

1. A method of inspecting balls within a ball grid array, the balls used as connections of integrated circuit modules, using an inspection apparatus having a microprocessor, a support for holding in place the modules to be inspected, wherein positioning of the support is controlled by the microprocessor, at least one camera connected to the microprocessor, the camera providing images of the balls, the balls being illuminated by a light source, said method comprising the steps of:

measuring a centrality of the grid array by taking views of successive adjoining sub-arrays of said grid array and combining said views to form a composite image of the module;

from said composite image, measuring the X and Y coordinates of each of the balls forming said grid array to determine a best fitting grid of said balls;

determining the Z coordinate measured from the top of each of said balls to define a best fitting plane applicable to said array, based on said best fitting grid;

offsetting said best fitting plane so that the plane includes the lowest ball of said array of balls;

computing a deviation in the Z direction between each of said balls of said array and said offset plane; and comparing the computed deviation against a predetermined specification and discarding as defective any said modules exceeding said first deviation and said deviation in the Z direction.

2. The method as recited in claim 1, wherein the step of determining the best fitting grid of said balls further comprises the steps of:

measuring the position of each of the balls of said array for each of said modules;

determining from the position of each of the balls the best fitting grid to best match all the balls of said array of balls; and computing the deviation in the x and y directions between each of said balls and its position within said best fitting grid.

3. The method as recited in claim 2, wherein said step of measuring the position of each of said balls in said array further comprises taking successive juxtaposed views with the camera of sections of said array of balls, each section comprising a sub-array of m by n of said balls.

4. The method as recited in claim 1, wherein the step of determining the Z coordinate of each of said balls of said array further comprises taking views with a tilted camera of successive juxtaposed rows of said array of balls, wherein said balls are illuminated by the light source placed opposite to said camera, and wherein the image of said balls taken by said camera corresponds to a light reflection at the top of said ball.

5. The method as recited in claim 1, wherein said step of determining the best fitting plane for said array of balls further comprises applying a Least Square Regression technique to the computation of parameters that define said plane so as to minimize the sum of squared distances between the plane and the balls.

6. The method as recited in claim 4, wherein the Z coordinate measured at the top of each of said balls and detected by the tilted camera is corrected by determining a deviation of the position of each of said balls with respect to a predetermined position in said best fitting grid.

7. The method as recited in claim 6, wherein prior to the step of detecting the Z coordinate of each of said balls, the relative position of the module with respect to the vertical camera is adjusted to account for the thickness of the module.

8. The method as recited in claim 1, further comprising a calibration step that includes a coarse and a fine calibration, said calibration being performed prior to inspecting the module, wherein a scale and a drift required by the inspection are defined.

9. The method as recited in claim 8, wherein said coarse calibration further comprises obtaining an image of said array of balls and computing an average of the deviation between said balls, wherein said balls are combined two by two to define a pixel scale.

10. The method as recited in claim 9, wherein said fine calibration further comprises:

determining the drift resulting from a misalignment between an axis of said camera and an axis of the support by computing the difference between the variation between two successive views of said balls taken by the camera and the slope of the module with respect to the support;

determining the X and Y scales by computing the ratio of the distance between said balls captured by said camera in one of said views to the distance between balls in two of said views, and determining the Z scale by using the angle 0 between the vertical plane and the image plane when a view is taken with a tilted camera.

11. A method of inspecting balls within a ball grid array, the balls used as connections of integrated circuit modules, using an inspection apparatus having a microprocessor, a support movable in the X and Y directions controlled by said microprocessor, first and second cameras coupled to said microprocessor for providing images of the balls, said method comprising the steps of:

a) measuring a centrality of the grid array by taking views of successive adjoining sub-arrays of said grid array and combining said views to form a composite image of the module;

b) combining said views to form an image of said array of balls;

c) from said image, measuring the position of each said balls, computing a best fitting grid and a first deviation in the X and Y directions between each of said balls and said best fitting grid;

d) determining the height of said balls with said second camera tilted with respect with said module, taking views of successive rows, while said balls are illuminated by a source of light placed opposite to said wherein an image of said balls in each said views corresponds to light reflections at the top of said balls;

e) computing a best fitting plane formed by said tops of said balls;

f) offsetting said best fitting plane by an amount determined by the top of the lowest of said balls in said array of balls to form an offset plane;

g) computing a deviation in the Z direction between said best fitting plane and said offset plane; and h) comparing said first deviation and said deviation in the Z direction with predetermined specifications, and discarding as defective any said modules exceeding said first deviation and said deviation in the Z direction.

12. The method as recited in step d) of claim 11, further comprising the step of correcting said height of said tops of said balls by adjusting said height in accordance with said first deviation.

13. The method as recited in step d) of claim 11, wherein said first camera is adjusted to account for the thickness of said module.

14. The method as recited in claim 11, wherein calibration is performed prior to said inspection to quantify a drift that occurs while taking said views.

15. The method as recited in claim 14, wherein said calibration includes a coarse and a fine calibration.

16. The method as recited in claim 15, wherein said coarse calibration includes creating an image of said array of balls and subsequently computing a deviation in the X and Y directions between two of said balls by combining said balls two by two to determine an approximate pixel scale.

17. The method as recited in claim 15, wherein said fine calibration further comprises the steps of:

determining said drift resulting from a misalignment between said first camera and said support by computing a difference between a variation from one of said views to the next of said views taken with said first camera and the tilt of said module with respect to said support;

determining X and Y scales by computing a ratio of the distance between balls of one of said views over the distance between balls of two of said views; and determining a Z scale by using an angle formed by a vertical plane and an image plane determined when a view is taken with said second camera.

* * * * *

UNITED STATES PATENT AND TRADEMARK OFFICE
CERTIFICATE OF CORRECTION

PATENT NO. : 5,574,801
DATED : November 12, 1996
INVENTOR(S) : Olivier Collet-Beillon It is certified that error appears in the above-indentified patent and that said Letters Patent is hereby corrected as shown below:

Title page, item [73], Assignee: insert--International Business Machines Corporation, armonk, N.Y.--.

Title page, before item [57], Abstract: insert the following:
-- Attorney, agent or Firm-- H. Daniel Schnurmann--.

Signed and Sealed this

Third Day of June, 1997

Attest:

BRUCE LEHMAN

*Attesting Officer*  *Commissioner of Patents and Trademarks*